(12) United States Patent
Shah et al.

(10) Patent No.: US 9,126,010 B2
(45) Date of Patent: Sep. 8, 2015

(54) DEVICE AND METHOD FOR FINDING THE CENTER AND READING THE SETTING OF AN IMPLANTABLE MEDICAL DEVICE

(71) Applicant: MEDTRONIC XOMED, INC, Jacksonville, FL (US)

(72) Inventors: Deep Shah, Santa Barbara, CA (US); Tony Daniel Cepeda, Santa Maria, CA (US); Lori Speckman, Ventura, CA (US); W. Jeff Bertrand, Ventura, CA (US); Lawrence Hampton, Santa Maria, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 247 days.

(21) Appl. No.: 13/826,727

(22) Filed: Mar. 14, 2013

(65) Prior Publication Data
US 2014/0261793 A1    Sep. 18, 2014

(51) Int. Cl.
*F16K 37/00* (2006.01)
*A61M 27/00* (2006.01)

(52) U.S. Cl.
CPC .......... *A61M 27/006* (2013.01); *Y10T 137/8225* (2015.04)

(58) Field of Classification Search
CPC ................. A61B 17/068; A61B 17/11; A61B 2017/0647; A61B 2017/1107; A61B 2017/0649; A61B 17/064; A61M 39/0208; A61M 39/0247; A61M 27/006
USPC ........................................ 128/899; 604/891.1
See application file for complete search history.

(56) References Cited

U.S. PATENT DOCUMENTS

| | | | |
|---|---|---|---|
| 4,676,772 A * | 6/1987 | Hooven | ............................ 604/9 |
| 5,637,083 A | 6/1997 | Bertrand et al. | |
| 5,643,194 A | 7/1997 | Negre | |
| 5,758,667 A | 6/1998 | Slettenmark | |
| 5,944,023 A | 8/1999 | Johnson et al. | |
| 6,050,969 A | 4/2000 | Kraus | |
| 6,138,681 A | 10/2000 | Chen et al. | |
| 6,234,956 B1 | 5/2001 | He et al. | |
| 6,391,019 B1 | 5/2002 | Ito | |
| 6,417,750 B1 | 7/2002 | Sohn | |
| 6,439,538 B1 | 8/2002 | Ito | |
| 6,657,351 B2 | 12/2003 | Chen et al. | |
| 6,702,249 B2 | 3/2004 | Ito | |

(Continued)

FOREIGN PATENT DOCUMENTS

| | | |
|---|---|---|
| DE | 102007059300 | 6/2009 |
| WO | 2009066133 | 5/2009 |
| WO | 2011136241 | 3/2011 |

OTHER PUBLICATIONS

International Search Report and Written Opinion for corresponding PCT Application No. PCT/US2014/027222 mailed Jun. 24, 2014.

*Primary Examiner* — Samuel Gilbert
(74) *Attorney, Agent, or Firm* — Dicke, Billig & Czaja, PLLC

(57) ABSTRACT

A centering tool and a combined centering-indicator tool for finding the magnetic center and indicating the setting of an implantable adjustable valve. The centering and combined centering-indicator tools include a magnetic capsule movable within a cavity to a target located on the tool when the magnetic capsule is centered over magnet of an adjustable valve.

18 Claims, 8 Drawing Sheets

(56) References Cited

U.S. PATENT DOCUMENTS

| | | |
|---|---|---|
| 6,840,917 B2 | 1/2005 | Marion |
| 6,951,059 B2 | 10/2005 | Moskowitz et al. |
| 7,057,369 B2 | 6/2006 | Hoffmann |
| 7,255,682 B1 | 8/2007 | Bartol, Jr. et al. |
| 7,334,582 B2 * | 2/2008 | Bertrand et al. .............. 128/899 |
| 7,334,594 B2 | 2/2008 | Ludin |
| 7,338,028 B2 | 3/2008 | Zimmerling et al. |
| 7,422,566 B2 | 9/2008 | Miethke |
| 7,485,105 B2 | 2/2009 | Wolf |
| 7,771,381 B2 | 8/2010 | McCusker et al. |
| 7,856,987 B2 | 12/2010 | Bertrand et al. |
| 7,921,571 B2 | 4/2011 | Moureaux et al. |
| 8,038,641 B2 | 10/2011 | Soares et al. |
| 8,057,422 B2 | 11/2011 | Wolf, II |
| 8,123,714 B2 | 2/2012 | Ludin et al. |
| 8,171,938 B2 | 5/2012 | Bengtson |
| 8,241,240 B2 | 8/2012 | Murphy |
| 8,322,365 B2 | 12/2012 | Wilson et al. |
| 8,398,577 B2 | 3/2013 | Burnett |
| 8,398,617 B2 | 3/2013 | Ginggen et al. |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 | 1/2014 | Negre et al. |
| 8,733,394 B2 | 5/2014 | Negre et al. |
| 8,753,331 B2 | 6/2014 | Murphy |
| 8,763,637 B2 | 7/2014 | Soldo et al. |
| 8,813,757 B2 | 8/2014 | Prisco et al. |
| 2001/0022350 A1 | 9/2001 | Ito |
| 2005/0022403 A1 * | 2/2005 | Moskowitz et al. ......... 33/355 R |
| 2005/0055009 A1 | 3/2005 | Rosenberg |
| 2007/0004999 A1 | 1/2007 | Miethke |
| 2008/0083413 A1 | 4/2008 | Forsell |
| 2009/0076597 A1 | 3/2009 | Dahlgren et al. |
| 2010/0199506 A1 | 8/2010 | Moureaux et al. |
| 2011/0048539 A1 | 3/2011 | Negre et al. |
| 2011/0066098 A1 | 3/2011 | Stergiopulos |
| 2011/0105991 A1 | 5/2011 | Roth et al. |
| 2011/0105992 A1 | 5/2011 | Girardin et al. |
| 2011/0105993 A1 | 5/2011 | Girardin et al. |
| 2011/0118589 A1 | 5/2011 | Negre et al. |
| 2011/0295104 A1 * | 12/2011 | Teitelbaum et al. ......... 600/409 |
| 2012/0029414 A1 | 2/2012 | Wolf, II |
| 2012/0046595 A1 | 2/2012 | Wilson et al. |
| 2012/0046596 A1 | 2/2012 | Ludin et al. |
| 2012/0197178 A1 | 8/2012 | Prisco et al. |
| 2013/0002243 A1 | 1/2013 | Bertrand et al. |
| 2013/0085441 A1 | 4/2013 | Aihara |
| 2013/0345646 A1 | 12/2013 | Bertrand et al. |
| 2014/0052047 A1 | 2/2014 | Wilson |
| 2014/0121586 A1 | 5/2014 | Bertrand et al. |
| 2014/0257166 A9 | 9/2014 | Wolf, II |
| 2014/0261793 A1 | 9/2014 | Shah et al. |
| 2014/0276340 A1 | 9/2014 | Ludin et al. |
| 2014/0276346 A1 | 9/2014 | Sadanand |

* cited by examiner

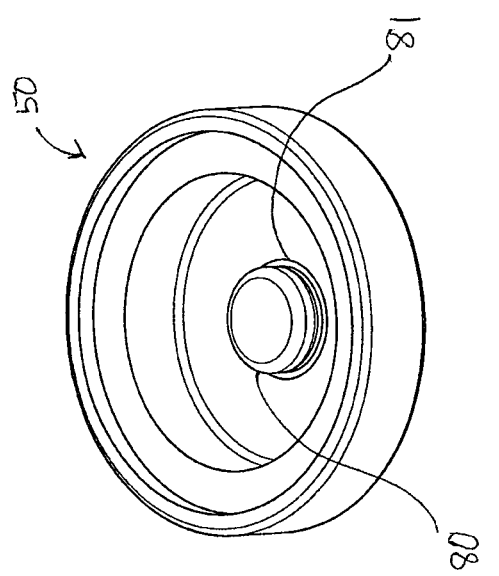

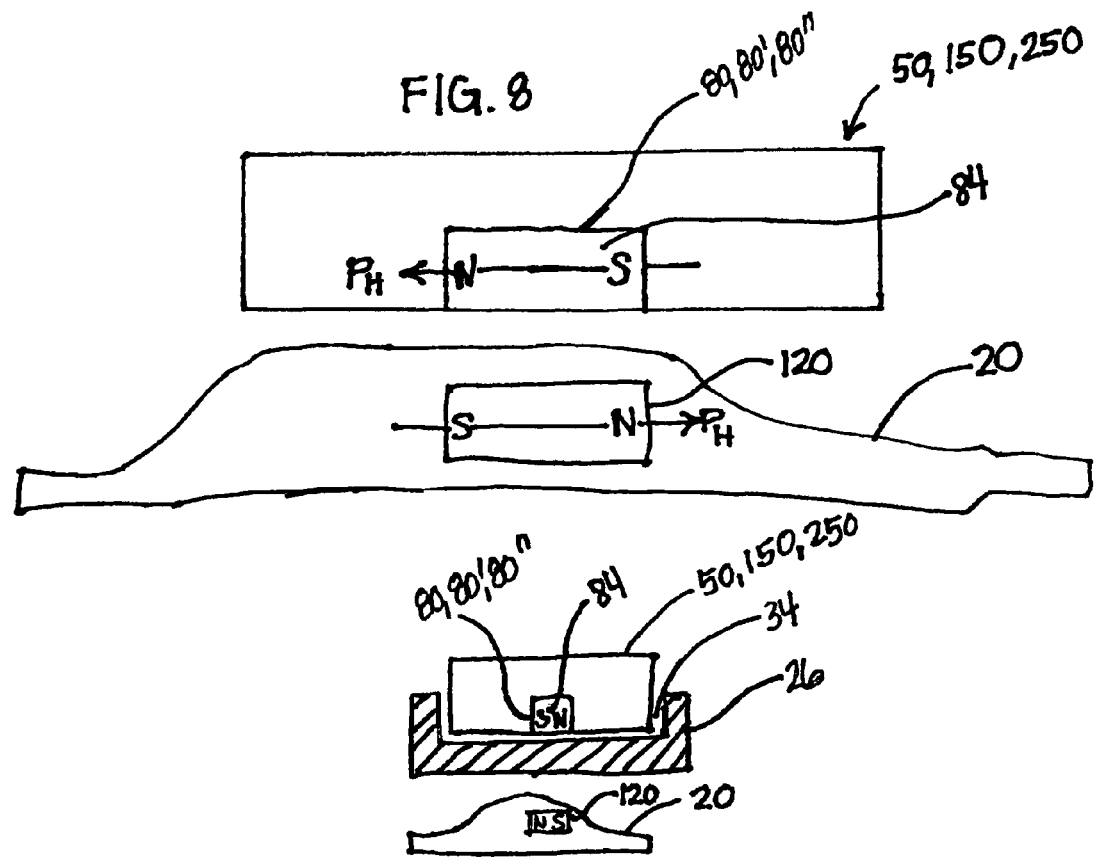
FIG. 8
FIG. 9A
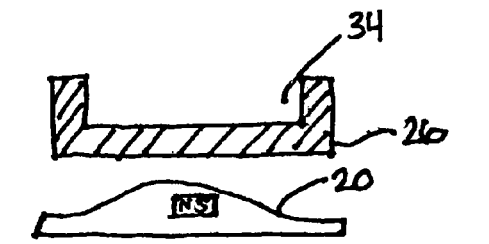
FIG. 9B
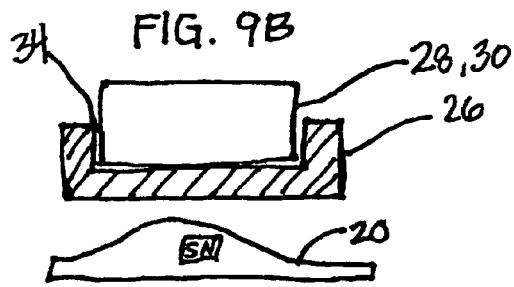
FIG. 9C

DEVICE AND METHOD FOR FINDING THE CENTER AND READING THE SETTING OF AN IMPLANTABLE MEDICAL DEVICE

BACKGROUND

The present disclosure relates to implantable medical devices such as fluid flow control devices including adjustable valves and also relates to tools for determining the location and settings of an adjustable valve. More particularly, the present disclosure relates to tools for finding the magnetic center and indicating a setting of an implantable adjustable valve.

Generally, a fluid flow control device includes a one-way control valve for controlling the flow of cerebrospinal (CSF) fluid out of a brain ventricle and preventing backflow of fluid into the brain ventricle. Hydrocephalus, a neurological condition which may affect infants, children and adults, results from an undesirable accumulation of fluids, such as CSF, within the ventricles, or cavities, of the brain and which accumulation may exert extreme pressure with brain and skull deforming forces, the latter in infants. Treatment of hydrocephalus often involves draining CSF away from the brain ventricles utilizing a drainage or shunt system including one or more catheters and a valve which may generally be described as a fluid flow control device or shunt valve. The shunt valve, or fluid flow control device, may have a variety of configurations and may be adjustable in that the valve mechanism of the device may be set to a threshold pressure level at which fluid may be allowed to begin to flow through the valve and drain away from the brain. Shunt valves may be subcutaneously implantable and percutaneously adjustable to various pressure settings. Examples of fluid flow control devices are disclosed, for example, in U.S. Pat. No. 5,637,083 entitled, "Implantable Adjustable Fluid Flow Control Valve", and U.S. patent application Ser. No. 13/804,875 entitled, "Fluid Flow Control Devices, Rotors and Magnets with Increased Resistance to Inadvertent Setting Change and Improved Accessory Tool Coupling", incorporated by reference herein in their respective entireties.

Adjustable valves may include magnetic components which allow an external tool or tools to selectively and non-invasively determine the setting of the implanted valve and adjust the setting to a desired pressure. A tool set typically includes: a locator tool, which allows tactile determination of the orientation and position of the implanted valve; an indicator tool, to determine the current setting of the adjustable valve and confirm new settings of the valve after the new settings have been implemented; and an adjustment tool to change the setting of the valve. The tools are designed to externally (i.e., external to a patient) couple with a magnet of the adjustable valve such that upon coupling, the setting of the valve may be determined and the valve magnet may be deliberately manipulated to thereby adjust the pressure setting of the valve without removal of the subcutaneously implanted device. Indicator and adjustment tools thus rely on magnetic coupling of the tool to the adjustable valve, where the magnetic coupling is strong enough to determine or to adjust the position of the valve magnet even through tissue (e.g., a patient's scalp). Examples of locator, indicator and adjustment tools are shown, for example, in U.S. Patent Application Publication No. 2002/0022793 (hereinafter, "the '793 application") to Bertrand et al. entitled, "Tool for Adjusting an Implantable Adjustable Fluid Flow Control Valve" and U.S. Pat. No. 6,883,241 to Moskowitz, et al., entitled, "Compass-Based Indicator with Magnetic Shielding", incorporated by reference herein in their respective entireties.

Locator, indicator and adjustment tools may be used in conjunction with one another. For example, after the tactile determination of a valve's position has been made in conjunction with a locator tool, an indicator and/or adjustment tool may be positioned in a location determined by the locator tool. In other words, an indicator and/or adjustment tool position may be based off of or may be "keyed to" the locator tool position. The position of an adjustable valve, as determined by the locator tool, allows the indicator and/or adjustment tools to be placed in sufficient proximity to the magnetic components of the implanted valve such that the valve magnet or magnets align and/or couple with the magnetized tool elements or magnets. However, the magnetized element of an indicator tool may tend toward alignment with the earth's magnetic field if the pull of the magnet in the implanted valve is not sufficiently strong (such as when the distance between the implanted valve magnet or magnets and the tool increases) and could lead to inaccurate device setting determinations or indications.

In addition, magnetic components of the adjustable valve itself may be susceptible to movement or inadvertent setting adjustment by strong nearby magnetic fields since the internal magnetic elements of a valve may tend to align with an external field. An adjustable valve might therefore be unintentionally adjusted when in the presence of a strong external magnetic field, such as encountered in a magnetic resonance imaging (MRI) procedure. Thus, some fluid flow control devices include features which provide increased resistance to inadvertent setting changes. For example, mechanical "stops" or magnet configurations designed to resist strong nearby magnetic fields may be incorporated into a device such as disclosed, for example, in U.S. patent application Ser. No. 13/804,875, referred to above. Deliberate adjustment of these types of valves, in some cases, may be more difficult to achieve without an accurate alignment of the adjustment tool to the valve magnet.

In order to accurately magnetically align or couple a tool to an implanted valve (for example, to avoid effects of the earth's magnetic field on the tool or to ensure a sufficient coupling of a tool to a valve for valve setting indication and adjustment purposes), it may thus be desirable to find the magnetic center of the valve magnet and thereby position a tool in magnetic alignment with the magnetic center of the valve magnet. Aligning an external tool with the magnetic center of the valve can provide coupling of the tool to the valve which allows an accurate or more accurate reading of a valve setting and allows deliberate adjustment of the valve to be carried out, even where the distance between the implanted valve and the external tool is increased, and/or in cases where an implantable valve is designed for increased resistance to inadvertent setting changes.

The '793 publication depicts examples of tools which may be useful with an adjustable valve and which may be used in conjunction with the centering and centering-indicator tools 50, 150, 250 (FIGS. 3, 6, 7) of the present disclosure. The '793 publication describes a locator tool comprising a tube with a central opening and a slot. An index on the tube is for visually indicating the settings of a valve, e.g., 20, when the locator tool is aligned with the valve. The locator tool also includes a protrusion extending inwardly into the central body as well as a fluid flow direction indicator. An indicator tool may comprise an indicator central body a compass having a magnetized pointer, an index for indicating possible positions of the adjustable valve corresponding to the different valve settings, and a ridge for interacting with the protrusion of the locator tool.

As further described in the '793 publication, the locator central opening allows locator tool to be oriented to and aligned with an implanted valve in a predictable manner and allows the physician to palpate the implanted valve through opening. In use, after orientation of the implanted valve has been established by locator tool, indicator central body is placed within tube of locator tool. Indicator and locator tools may comprise alignment features. For example, when indicator central body is placed within tube, a ridge of the indicator tool aligns and interacts with a slot of the locator tool to precisely orient the indicator tool with the locator tool. Other alignment features of the indicator and locator tools are contemplated. In any event, placement of indicator tool into locator tool allows the indicator tool pointer to interact with and align itself with the magnet 120 of the valve 20. This will cause the pointer to point to a spot on the index indicating the position of the magnet 120 of the valve 20. The position of the magnet 120, as described above, indicates the setting of the valve.

The '793 publication further describes an adjustment tool having a magnet fixed in place in an adjustment central body, an indentation and an arrow. Adjustment central body may include a series of indentations configured to interact with a protrusion on the locator tool. Indentations may be spaced around the periphery of the adjustment central body corresponding to the location of the settings of the valve 20. In use, the adjustment tool is positioned above the locator tool with the arrow aligned with the pressure level setting on index, the pressure level setting of the valve having been determined previously by the indicator tool as described above or by other methods such as x-ray or fluoroscopy. Maintaining alignment, the adjustment tool is lowered toward the locator tool until the adjustment central body enters the tube. Where an indicator tool has been used to determine the valve setting, the indicator tool is removed prior locating the adjustment tool into the locator tool. The protrusion on the locator tool interacts with an indentation on the adjustment central body corresponding to the current valve setting. In this position, the adjustment tool magnet couples with the valve magnet and the adjustment tool is rotated so that the arrow points to the desired valve setting indicated on index.

Other examples of devices for locating, indicating and adjusting the setting of an adjustable valve are described in U.S. Pat. No. 7,334,582 to Bertrand, et. al., "Electronic Valve Reader", U.S. Pat. No. 8,015,977 to Bertrand, et. al., "Indicator Tool for Use with an Implantable Medical Device", and U.S. Pat. No. 8,257,296 to Bertrand et. al., "System Including an Implantable Medical Device and Electronic Valve Indicator and Locator Device", incorporated by reference herein in their respective entireties.

U.S. Pat. No. 7,921,571 to Moureaux et al., "Device for Mechanically Locating and Reading the Setting of An Adjustable Valve" proposes a device for mechanically and reading the setting of an adjustable magnetic valve which describes a three-dimensionally pivoting compass including a needle and pin mounted on a pivot.

SUMMARY

Devices according to the disclosure include a centering tool having a housing including a cavity and a magnetic capsule disposed in the cavity where the magnetic capsule comprises a tool magnet. The magnetic capsule is configured to move within the cavity to center within a target on the tool when the tool magnet is magnetically aligned with a magnet of an adjustable valve.

In some embodiments, a combined centering-indicator tool includes a housing including a cavity and an index on the housing comprising adjustable valve setting values, a magnetic capsule disposed within the cavity comprising a tool magnet and a pointer, and a target. The magnetic capsule is configured to move within the cavity to center itself within the target when the tool magnet is magnetically aligned with the magnetic center of the adjustable valve magnet and can rotate with respect to an axis of the capsule such that the pointer rotates to point to a valve setting value on the index.

In some embodiments, a system includes a locator tool having a tube for receiving a centering tool or a combined centering-indicator tool, the centering tool or combined-centering tool including a housing and a cavity, a magnetic capsule disposed within the cavity and a target provided on the centering or centering-indicator tool, where the magnetic capsule is configured to move within the cavity to center itself within the target when the tool magnet is magnetically aligned with the magnetic center of an adjustable valve magnet, the magnetic capsule also configured to rotate within the cavity. Where the tool includes an index and a pointer on or part of the magnetic capsule, rotation of the magnetic capsule may allow the pointer to rotate to point to a valve setting value on the index when the tool magnet is aligned with the valve magnet. The centering or combined centering-indicator tool is configured to be positioned within the tube of the locator tool when the locator tool is in proximity to the implanted adjustable valve.

In some embodiments including those described above, the magnetic capsule can be visible through a wall of the housing and may comprise a magnetic capsule housing having various shapes including a circular or disk-like shape. The tool magnet may include one or more magnets and each magnet may include vertical or horizontal polarity. Tool magnets of the present disclosure can also include a metal strip or strips or a Halbach array for strengthening the magnetic field to a side of the tool magnet. The target may have a perimeter substantially the same size as or slightly larger than the perimeter of the magnetic capsule or the magnetic capsule housing. A fluid may be disposed within the cavity and the magnetic capsule may move within the fluid.

BRIEF DESCRIPTION OF THE DRAWINGS

FIG. 3B is a perspective view of the centering tool of FIG. 3 with a magnet capsule in a position within the centering tool.

FIG. 8 is a side view illustration of a tool and an adjustable valve.

FIG. 9A is a cross-sectional side view illustration showing a step in a method of using a tool according to an embodiment.

FIG. 9B is a cross-sectional side view illustration showing a step in a method of using a tool according to an embodiment.

FIG. 9C is a cross-sectional side view illustration showing a step in a method of using a tool according to an embodiment.

DETAILED DESCRIPTION

The present disclosure provides centering and combined centering-indicator tools (e.g., 50, 150, 250 FIGS. 3, 6, 7) which may be used cooperatively or in conjunction with other tools such as a locator tool, an indicator tool or an adjustment tool. Centering and combined centering-indicator tools disclosed herein may also be used individually or in paired relationships with locator, indicator or adjustment tools as further explained hereinafter. In addition, the tools described herein may be useful with a variety of medical devices including, but not limited to, a variety of implantable magnetically adjustable valves which may or may not include features designed to provide resistance to inadvertent setting changes.

Figure 1:
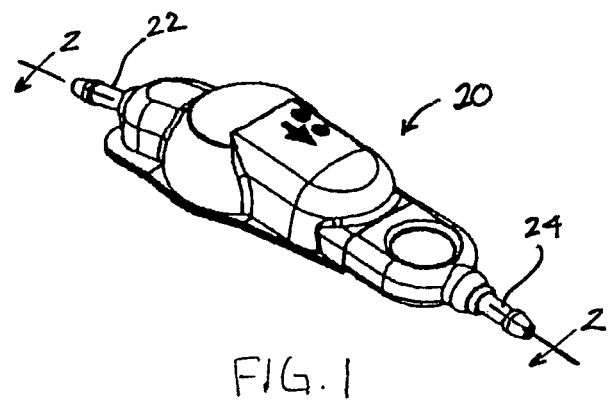
FIG. 1 is a perspective view of an adjustable flow control valve.
Figure 2:
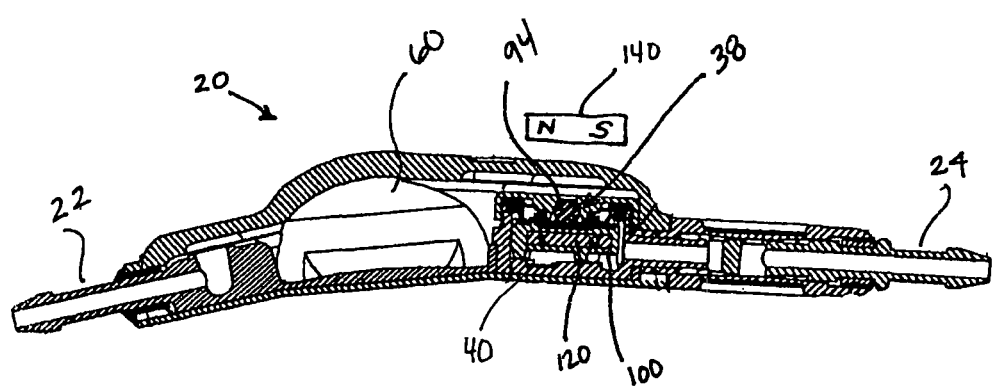
FIG. 2 is a side cross-sectional view of the valve of FIG. 1.

FIG. 1 depicts one example of a fluid flow control device 20, which may be useful with or used in conjunction with the centering and centering-indicator tools (50, 150, 250, FIGS. 3, 6, 7) of the present disclosure. Fluid flow control device 20 includes an inlet connector 22, configured to fluidly connect to a catheter (not shown) which may be inserted through a patient's skull into a brain ventricle containing CSF under pressure, and an outlet connector 24, configured to fluidly connect to a distal catheter which serves to direct CSF to another location in the patient's body. FIG. 2 depicts a cross-sectional view of the fluid flow control device of FIG. 1 taken along section 2-2, and an external tool 140 positioned above the device 20. Fluid flow control device 20 includes a fluid reservoir 60, a valve mechanism 38, and a rotor assembly 100. Rotor assembly 100 includes a valve magnet 120 or magnets and is configured to rotate in response to an applied magnetic field such as when encountering a magnetic tool 140.

As also described in U.S. patent application Ser. No. 13/804,875, the rotor magnet 120 may include a single magnet or dual magnets with horizontally or vertically aligned polarity. Rotor assembly 100 may be provided within a cartridge assembly 40 and may include an element such as a groove or a notch (not shown) which interacts with an element on a portion of the cartridge assembly 40 such as a spline or a tab (not shown). By including a particular magnet orientation or interacting elements on the rotor assembly 100 and cartridge assembly 40, the rotor assembly 100 may have an increased resistance to undesired rotation and therefore the valve 20 may have an increased resistance to inadvertent pressure setting changes, such as when a patient having an implanted valve is in the presence of a strong magnetic field (e.g., an MRI device).

As described above, it may be desirable to locate the center of the valve magnet 120 prior to making a valve setting determination and/or prior to adjusting the valve setting. As also described above, finding the magnetic center of valve 20 may serve to more easily, accurately or precisely align and couple an external tool 140 to the valve. The remaining Figures depict embodiments of centering and centering-indicator tools and tool elements useful with devices (e.g., adjustable valves) and/or useful with various locator, indicator or adjustment tools.

Figure 3:
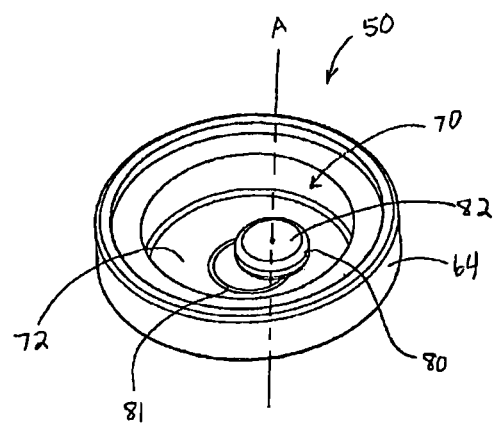
FIG. 3 is a perspective view of a centering tool.
Figure 3A:
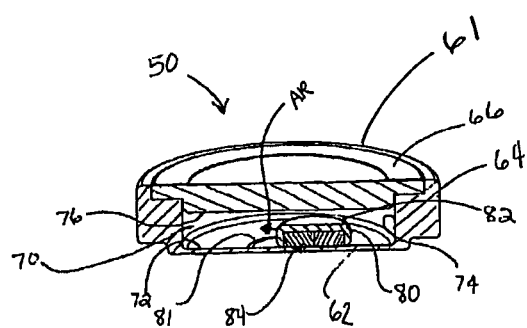
FIG. 3A is a side cross-sectional view of the centering tool of FIG. 3.

FIGS. 3 and 3A depict a centering tool 50. Centering tool 50 includes a housing or container 61, which is depicted in FIGS. 3, 3A as having circular disk shape. However, housing 61 may comprise various other shapes and configurations including circular, spherical, polygonal or other shapes. Nevertheless, housing 61 includes a housing bottom wall 62, side walls 64, upper wall 66 and a cavity 70. Cavity 70 is defined by a cavity floor 72, cavity side walls 74 and a cavity top or ceiling 76. Cavity 70 may be filled with a substance such as an oil or other liquid (not shown), for example, a mineral oil or other fluid, for example any fluid which may be useful as a compass oil. A dense fluid may be used so as to provide buoyancy to the magnetic capsule 80 or allow for the magnetic capsule 80 to be neutrally buoyant. For example, a perfluorochlorcarbon may be used. Other fluids are also contemplated.

Figure 4:
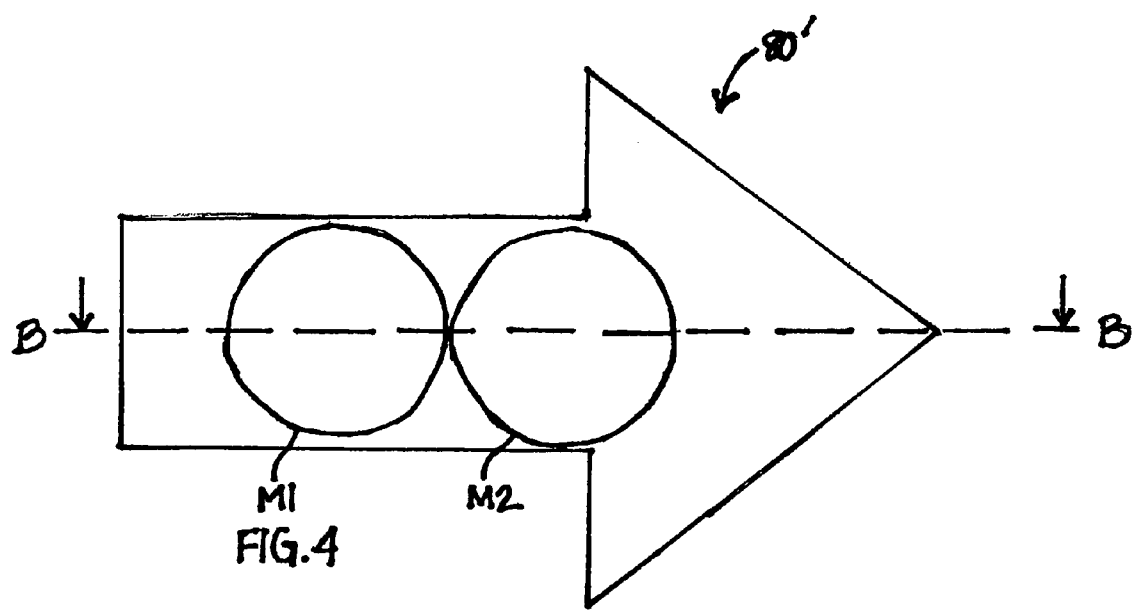
FIG. 4 is a top view of a magnet capsule according to an embodiment.

Provided within cavity 70 is a magnetic capsule 80 and a target 81. In general terms, magnetic capsule 80 (also 80', 80", FIGS. 3, 4, 6, 7 hereinafter generally referred to as magnetic capsule 80), is configured to move (e.g., slide) within cavity 70 and center itself within the target 81 when the target 81 of the centering tool 50 is centered over a valve magnet (e.g., valve magnet 120 of valve 20). Magnetic capsule 80 is configured to freely move within cavity 70 (e.g., in a lateral or rotational manner as explained below) such that magnetic capsule 80 is not connected or attached to any portion of cavity 70. Magnetic capsule 80 may thus slide freely within cavity 70. Use and operation of the centering tool 50 will be further described below. Magnetic capsule 80 may be constructed in a variety of configurations and may, for example, include a capsule housing 82 for encapsulating or housing one or more tool magnets 84. Alternatively, capsule 80 may be constructed with no housing 82 (i.e., tool magnet 84 does not include a housing 82). In still further alternative embodiments, housing 82 may be provided on or around only a portion of magnet 84, for example, only a bottom portion, a top portion, a side portion, or a combination thereof, of magnet 84. Magnetic capsule 80 may comprise a variety of spherical, cylindrical, polygonal, or other shapes including an arrow-shape, such as depicted in FIG. 4. The configuration or shape of capsule 80 may be defined by the shape of the tool magnet 84 or magnets (i.e., may be defined by the magnet configuration), or may defined by the shape of housing 82 in which the tool magnet or magnets 84 may be encapsulated, enclosed or otherwise provided within. Thus, for example, the form of the magnet configurations 91, 93, 95, 97 (FIGS. 5A-5E) themselves may define the shape of capsule 80. Or, capsule 80 may be in the form of housing 82, such as magnetic capsules 80, 80', and 80" (FIGS. 3, 4, 6, and 7).

Figure 5A:
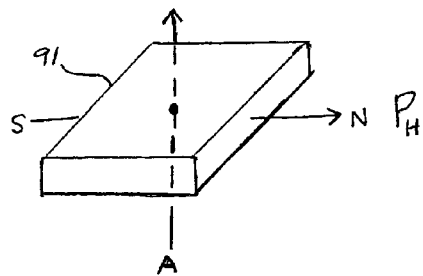
FIGS. 5A-5F are illustrations of magnet configurations.
Figure 5B:
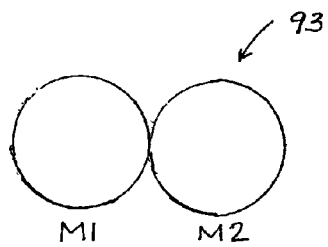
Figure 5C:
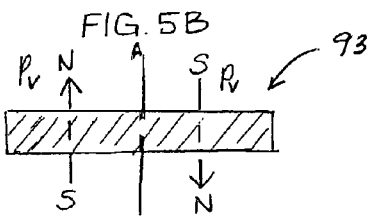

Tool magnet 84 may likewise comprise several different magnet configurations. Some non-limiting examples of the magnet configurations contemplated by the present disclosure are depicted in FIGS. 5A-5F. FIG. 5A depicts one embodiment of a magnet including a single magnet 91 having a squared shape and including a horizontal magnet polarity $P_H$ where the direction of polarity is perpendicular to a vertical magnet axis A. Alternatively, single magnet 91 could comprise other shapes such as a circular (for example magnet 84 as depicted in FIG. 4), spherical, polygonal or other shape. FIG. 5B is a top view of another embodiment of a magnet. Magnet 93 comprises two magnets M1, M2, adjacent one another. FIG. 5C is side view of magnet 93. Magnets M1 and M2 of FIGS. 5B and 5C are depicted as circular disks but may alternatively comprise several other shapes such as described with reference to FIG. 5A (e.g., spherical, square etc.). Magnet 93 may comprise horizontal polarity, as described above with respect to magnet 91 of FIG. 5A, or magnets M1 and M2 may comprise vertical polarity $P_V$ (FIG. 5C) such that polarity of each magnet is parallel to a vertical magnet axis A. For example, as described in the U.S. patent application Ser. No. 13/804,875, including vertically polarized magnets in a device can provide a device having a reduced tendency to undesirably align with a magnetic field. Thus, if magnet 84 (FIGS. 3, 6, 7) includes vertical polarity, magnet 84 (and therefore magnetic capsule 80) may have less tendency to align with an external magnetic field, (such as that created by an MRI device or such as the Earth's magnetic field).

Figure 5D:
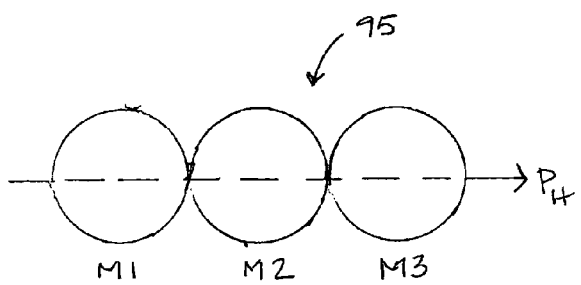

FIG. 5D is a top view of another embodiment of a magnet depicting magnet 95 comprising three magnets M1, M2, M3 having a horizontally aligned polarity $P_H$. Magnets M1, M2 and M3 are depicted as spherical or ball-shaped magnets, however, as described with reference to FIGS. 5A and 5B, magnets M1-M3 may likewise include other shapes or geometries.

Figure 5E:
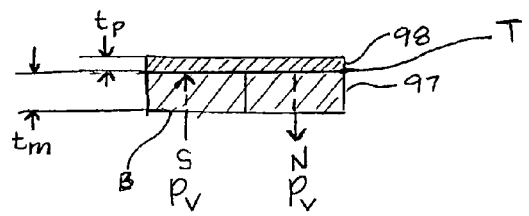
Figure 5F:
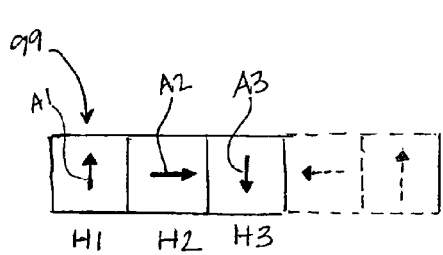

FIG. 5E shows a side view of another embodiment of a magnet depicting a magnet 99 comprising two magnets, M1 and M2 having vertical polarity $P_V$ and a strip or element 98 disposed on the top "T" of the magnet 99. As with magnets 91, 93, and 95, magnets M1 and M2 of magnet 97 may alternatively include horizontal polarity and may include any of the various shapes described above. Strip 98 has a thickness "$t_p$" and may comprise metal and for example may comprise steel. Strip 98 may be attached to magnets M1, M2 via magnetic attraction between the two. Strip 98 may be constructed of a ferromagnetic material such as iron or steel and the thickness "$t_p$" of strip 98 may be less than a thickness "$t_m$" of magnet 99 and may in some embodiments comprise a thin metal magnet. Providing strip 98 at the top of magnet 97 may effectively weaken the magnetic field at the top "T" of magnet 97 while strengthening the magnetic field toward the bottom "B" of magnet 97. This strengthening of the magnetic field at the bottom of magnet 97 may allow for better coupling of tool 140 to valve magnet 120 of an implanted valve 20. Another magnet configuration is shown in FIG. 5F. Magnet 99 comprises a Halbach array which includes magnets H1, H2, H3 having magnetization illustrated for each magnet by arrows A1, A2, A3. The Halbach array may include additional magnets, such as shown in FIG. 5F in phantom, with magnetization of each magnet rotated with respect to an adjacent magnet in a pattern as known for Halbach arrays. It is to be understood that any number of magnets may be utilized with the Halbach array. As is known, a Halbach array augments a magnetic field on one side of the array while cancelling the field to near zero on the other side via the spatially rotating pattern of magnetization of the magnets of the array. Thus, providing a magnet 99 configured as a Halbach array may strengthen the magnetic field below the array and serve to create a stronger coupling of magnet 99, and thereby magnetic capsule 80, to a valve magnet 120.

Returning to FIG. 3, housing 82 may comprise a variety of suitable materials including metals or polymers or combinations thereof and specifically non-magnetic materials. In some embodiments, the housing material is clear, transparent or see-through whereby magnetic capsule 80 is visible through housing 82 (and in some embodiments, in particular, through housing upper wall 66), such as depicted in FIGS. 3, 4, 6 and 7. In addition, a portion or portions of housing 82 may be constructed of one material while another portion or portions of housing 82 may be constructed of another or different material. Regardless, the material of housing 82 may be designed to allow for ease of movement of magnetic capsule 80 within cavity 70. Thus, housing 82 may be constructed of a material designed to reduce friction between magnetic capsule 80 and cavity walls 72, 74 and 76. For example, housing 82 may be constructed of PTFE, acetal or other materials.

Magnetic capsule 80 may be configured to slidably move, float or suspend within cavity 70 and may be configured to rest on or float just above cavity floor 72 or may be configured to be suspended within cavity 72 at any distance between cavity floor 72 and cavity top or ceiling 76. In some embodiments the space between the magnetic capsule and the floor 72 is limited and configured to be as small as possible so as to keep the magnetic capsule 80 as close to the floor 72 as possible thereby providing a closer relationship between the magnetic capsule 80 and the valve magnet 120. Regardless, magnetic capsule 80 is configured to center within a target 81 when positioned over the magnetic center of a magnet (e.g., 120, FIG. 1) of an adjustable valve (e.g., 20, FIG. 1). Target 81 comprises a marking at a location on the tool 50 such as on the floor 72 or ceiling 76 of cavity 70, other positions for target 81 are also contemplated. The target 81 is located on device 50 such that when the approximate center of the device 50 is centered over a valve magnet 120, the tool magnet 84 or magnetic capsule 80 will move laterally with respect to cavity floor 72, to the center or approximate center of the target 81. Thus, in an embodiment, capsule 80 may slide along or just above the floor 72 of cavity 70 until capsule 80 is centered over the valve magnet 120 of an implanted valve at which point the magnetic attraction between the tool magnet 84 and valve magnet 120 causes the magnetic capsule to center within the target 81. For example, a user may move the device 50 until magnetic capsule 80 is substantially centered within target 81, indicating that the device 50 is approximately centered over the valve magnet 120. Magnetic capsule 80 may also rotate (i.e., spin) with respect to a magnetic capsule axis A' within cavity 70, when the tool magnet 84 aligns with the valve magnet 120. In this manner, magnetic capsule 80 may indicate a device 20 setting as further described below.

Target 81 may have a shape which is substantially the same as the shape of magnet 84 or magnetic capsule 80. The target 81 may include a line or a solid (i.e., "filled-in") shape and may have an outer periphery, perimeter or edge which is the same as or slightly larger than that of the tool magnet 84 or magnetic capsule 80. Where the target 81 comprises an outer periphery that is approximately the same size as the outer perimeter of the magnetic capsule 80, the target 81 will essentially be covered or obscured. Where the target 81 includes an outer periphery that is larger than the outer perimeter of the magnetic capsule, as can be seen in FIG. 3B, when the magnetic capsule 80 is centered over the valve magnet 120, magnetic capsule 80 will move to the center of the target 81. For example, magnetic capsule 80 of FIG. 3A moves in the direction of arrow (AR) to the position shown in FIG. 3B. In FIG. 3B, the outer edge of target 81 can be seen surrounding the centered magnetic capsule 80, thereby indicating to a user that the tool 50 is centered over a valve magnet 120. Similarly, where the perimeter of target 81 is the same size as or smaller than the perimeter of the tool magnet 84 or magnetic capsule 80, covering of the target 81 would indicate to a user that the tool magnet and/or magnetic capsule 80 and therefore the tool 50 is centered or approximately centered over the valve magnet 120.

Figure 4A:
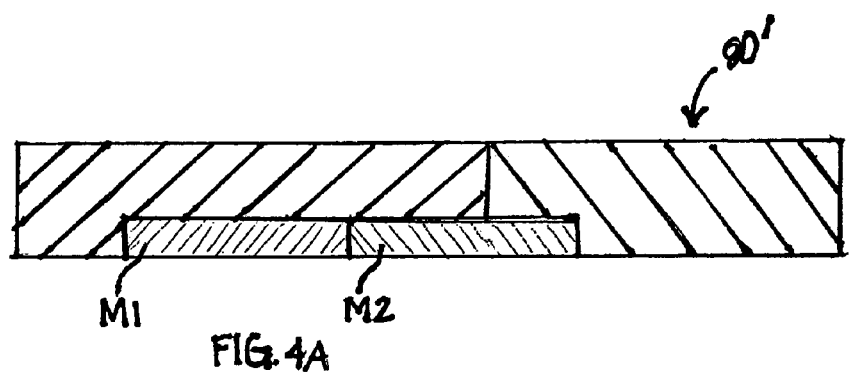
FIG. 4A is a side cross-sectional view of the magnet capsule of FIG. 4.

FIGS. 4 and 4A depict another embodiment of a magnetic capsule. Magnetic capsule 80' comprises an arrow-shape and magnets M1, M2 provided in the capsule 80'. FIG. 4A is a cross sectional view of magnetic capsule 80', taken along line B-B of FIG. 4. As described above, target 81 may comprise an arrow shape (not shown) such that magnetic capsule 80' may position itself within the target 81 arrow (not shown) when magnets M1, M2 are positioned over the center of a valve magnet) e.g., 120. The arrow-shape may advantageously indicate a setting of device 20 such that rotation of magnetic capsule 80 aligns the tool magnet or magnets 84 with the valve magnet 120 causing the arrow to point to a setting on the centering tool (e.g., 150, 250) or locator tool 26 (FIGS. 9A-9C).

Figure 6:
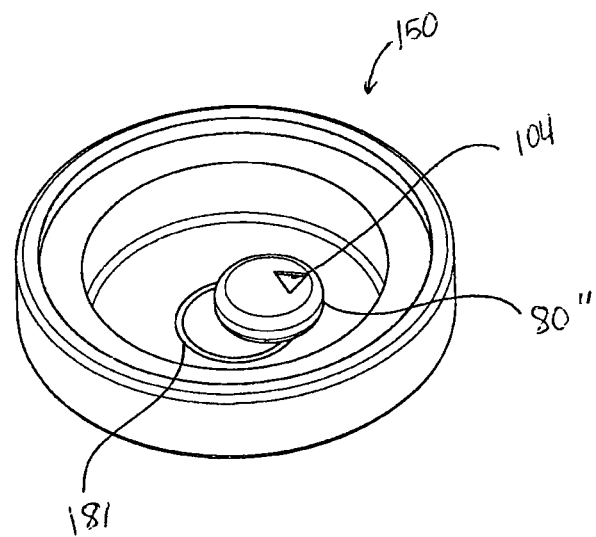
FIG. 6 is a perspective view of a combined centering-indicator tool.
Figure 6A:
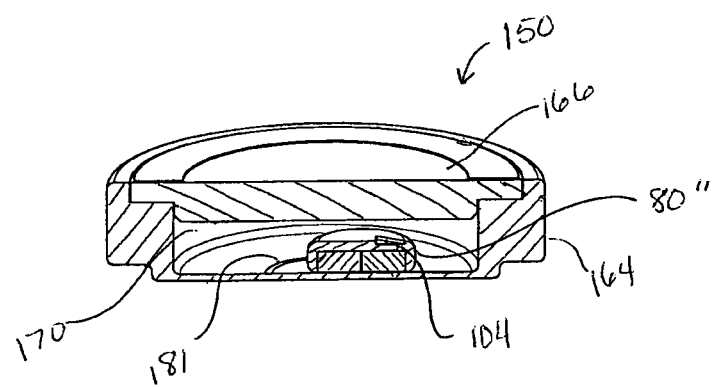
FIG. 6A is a side cross-sectional view of the combined centering-indicator tool of FIG. 6.

FIGS. 6 and 6A show an embodiment of a combined centering-indicator tool. Centering-indicator tool 150 is similar to centering tool 50 with like numerals representing like features. As with tool 50, magnetic capsule 80" is provided within cavity 170 and is configured to center within a target 181 when the magnetic capsule 80" is centered over a valve magnet (e.g., 120). However, as depicted in FIGS. 6 and 6A, magnetic capsule 80" further includes a pointer 104. Pointer 104 104 is configured to point to a valve setting on an index provided on a locator tool (not shown). Thus, when the centering-indicator tool 150 is used in conjunction with a locator tool (not shown), magnetic capsule 80" will interact and align itself with a magnet (e.g., 120) of a valve (e.g., 20). This will cause the pointer 104 to point to a spot on an index of a locator tool (not shown) indicating the position of the magnet of the valve and thereby will indicate the valve setting. Described another way, magnetic capsule 80 moves axially to target 181 while also rotating or spinning to align with magnet 120 causing pointer 104 to point to the current setting of the adjustable valve 20.

Figure 7:
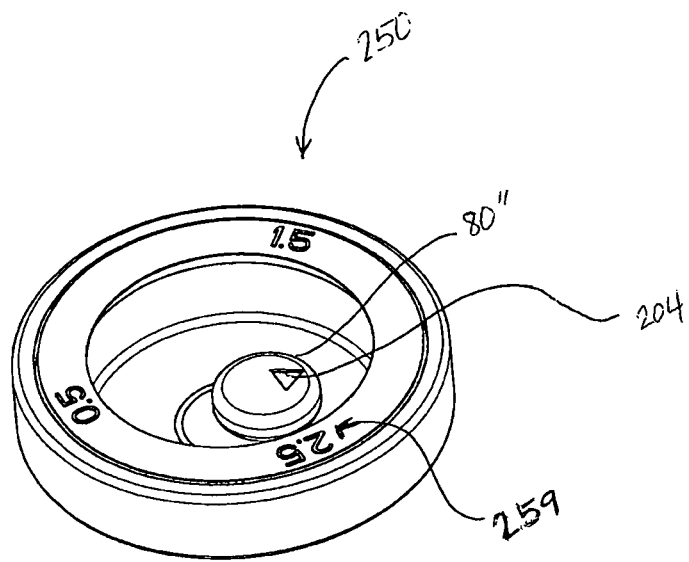
FIG. 7 is perspective view of a combined centering-indicator tool.
Figure 7A:
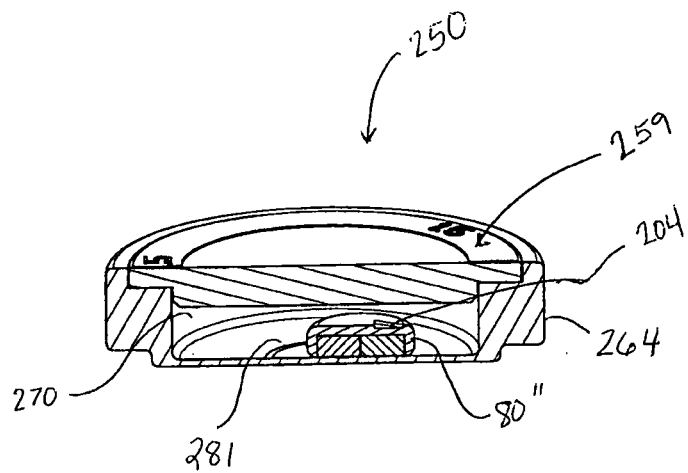
FIG. 7A is a side cross-sectional view of the combined centering-indicator tool of FIG. 7.

FIGS. 7 and 7A show another embodiment of a combined centering-indicator tool. Combined centering-indicator tool 250 is similar to tool 150 (FIGS. 6, 6A) however, tool 250 includes an index 259. Thus, in use, when magnetic capsule 80" interacts and align itself with a magnet (e.g., 120) of a valve (e.g., 20) and moves to or centers within the center of target 281, the interaction will also cause magnetic capsule 80" to rotate or spin causing pointer 204 to point to a spot on index 259 indicating the position of the valve magnet 120 and thereby indicating the valve setting.

FIG. 8 shows an example of the interaction between a valve magnet 120 and a magnet 84 of a magnetic capsule (e.g., 80, 80', 80"). In FIG. 8, tool magnet 84 is shown as comprising a horizontal polarity $P_H$. As described above however, vertical polarity of tool magnet 84 is likewise contemplated. Regardless, as shown in FIG. 8, placement of tool (e.g., 50, 150, 250) above valve 20, causes magnet 84 to magnetically align with valve magnet 120 thereby locating magnetic capsule 80, 80', 80" (and thus tool 50, 150, 250) in alignment with the valve magnet 120. For ease of illustration, additional features of tools 50, 150, 250 such as a target (e.g., 81) and cavity (e.g., 70) are not shown. In addition, as described above, magnet 84 may be comprised of one or more magnets and the overall effect of the magnetic field of the one or more magnets may be as depicted in FIG. 8.

An exemplary use of tools 50, 150, 250 is illustrated in FIGS. 9A-9C. FIG. 9A depicts a first step wherein a tool 50, 150 or 250 may be placed within a tube 34 of a locator tool 26 which has been previously oriented and aligned with an implanted valve 20 in a similar manner to the locator tool of the '793 publication, described above. Locator tool 26 may include a locator central opening (not shown) through which at least a portion of the valve 20 is palpated. As a second step, after magnetic capsule 80, 80', 80" centers over valve magnet 120, as illustrated in FIG. 9A, tool 50, 150, 250 may be removed from locator tool 26 such as depicted in such as depicted in FIG. 9B. As described above with reference to locator, indicator and adjustment tools of the '793 application, locator tool 26 and tools 50, 150, 250 may include interacting alignment features such as grooves, tabs, ridges or slots (not shown) on the outer surface of the tool 50, 150, 250 and inner surface of the locator tool 26 such that a tool 50, 150, 250 may be mechanically engaged with the locator tool 26. In any event, after the centering tool 50 or combined centering-indicator tool 150, 250 has identified the center of the valve magnet 120 (i.e., via tool magnet 84 or magnetic capsule 80, 80', 80" moving to a target (not shown) as described above), the tool 50, 150, 250 is removed from the locator tool 26 while the locator tool is held in the position identified by step one. As a third step, an adjustment tool 30 may then be placed within the tube 34 of the locator tool 26, such as shown in FIG. 9C. Alternatively, if a centering tool 50 was used to indicate the center of the valve magnet 120 (i.e., no combined centering-indicator tool was used in step one), step three may include placement of an indicator tool 28 for indicating the setting of a valve and a further step four (not shown) may include removal of the indicator tool and placement of an adjustment tool 30 in a similar manner as placement of a tool such as depicted in FIG. 9C. In other words, if a centering tool 50 is used to find the magnetic center of a valve magnet 120, subsequent use of a setting indicator and/or adjustment tool may be carried out in a manner similar to that described in the '793 application. Alternatively, if a combined centering-indicator tool (e.g., 150, 250) is utilized to find the magnetic center of an implanted valve 20 (i.e., find the center of magnet 120), and in conjunction with finding the center of the valve magnet 120, also indicates the current valve setting via pointing to an index (e.g., 259, FIG. 7) on the tool 250 or an index (not shown) on a locator tool 26 only an adjustment tool, or third step (FIG. 9) would be required.

Although the present disclosure has been described with reference to particular embodiments, workers skilled in the art will recognize that changes can be made in form and detail without departing from the spirit and scope of the present disclosure.

What is claimed is:

1. A centering tool for finding the center of an adjustable valve, the tool comprising:
    a housing including a cavity;
    a magnetic capsule comprising a tool magnet, the magnetic capsule disposed within the cavity;
    a target comprising a marking located on the centering tool;
    wherein the magnetic capsule is configured to slide within the cavity and center within the target when the tool magnet is magnetically aligned with a magnet of an adjustable valve.

2. The centering tool of claim 1, wherein the housing includes an upper wall and wherein the magnetic capsule is visible through the upper wall.

3. The centering tool of claim 2, wherein the housing comprises a circular-disk shape.

4. The centering tool of claim 3, wherein the tool magnet comprises two magnets.

5. The centering tool of claim 4, wherein each of the two tool magnets comprise vertical polarity with respect to an axis of the magnetic capsule.

6. The centering tool of claim 5, wherein the magnetic capsule comprises a disk-shape magnetic capsule housing.

7. The centering tool of claim 6, wherein the target comprises a circle having a perimeter larger than a perimeter of the magnetic capsule housing.

8. The centering tool of claim 7, further comprising a fluid contained within the cavity.

9. The centering tool of claim 8, wherein the magnetic capsule comprises a magnetic capsule housing.

10. The centering tool of claim 9, wherein the magnetic capsule housing comprises an arrow shape.

11. The centering tool of claim 1, wherein the magnet comprises a Halbach array.

12. The centering tool of claim 1, further comprising a metal strip disposed on the top of the tool magnet, wherein the metal strip comprises a thickness less than a thickness of the tool magnet.

13. The centering tool of claim 1, wherein the magnetic capsule is configured to slide along the floor of the cavity.

14. A combined centering-indicator tool for finding the magnetic center and indicating the setting of an adjustable valve, the tool comprising:
- a housing including a cavity and an index comprising valve setting values;
- a magnetic capsule comprising a tool magnet and a pointer, the magnetic capsule disposed within the cavity;
- a target comprising a marking located on the centering tool;
- wherein the magnetic capsule is configured to move within the cavity to center itself within the target when the tool magnet is magnetically aligned with the magnetic center of the adjustable valve magnet; and
- wherein the magnetic capsule is configured to rotate with respect to a magnetic capsule axis such that the pointer rotates to point to a valve setting value on the index.

15. The combined centering-indicator tool of claim 14, wherein the housing includes an upper wall and wherein the magnetic capsule is visible through the upper wall.

16. The combined centering-indicator tool of claim 15, wherein the target comprises a shape substantially similar to a shape of the magnetic capsule and wherein the outer perimeter of the target is larger than the outer perimeter of the magnetic capsule.

17. The centering tool of claim 15, further comprising a fluid contained within the cavity.

18. A system for finding the magnetic center and indicating the setting of an implanted adjustable valve, the system comprising:
- a locator tool comprising a tube;
- a combined centering-indicator tool comprising
  - a housing including a cavity and an index comprising valve setting values;
  - a magnetic capsule comprising a tool magnet and a pointer, the magnetic capsule disposed within the cavity;
  - a target disposed in the cavity;
  - wherein the magnetic capsule is configured to move within the cavity to center itself within the target when the tool magnet is magnetically aligned with the magnetic center of the adjustable valve magnet; and
  - wherein the magnetic capsule is configured to rotate with respect to a magnetic capsule axis such that the pointer rotates to point to a valve setting value on the index;
- wherein the combined centering-indicator tool is configured to be positioned within the tube of the locator tool when the locator tool is in proximity to the implanted adjustable valve.

* * * * *